(12) United States Patent
Lee et al.

(10) Patent No.: US 7,559,251 B2
(45) Date of Patent: Jul. 14, 2009

(54) APPARATUS FOR FORMING THERMAL FATIGUE CRACKS

(75) Inventors: Bo-Young Lee, 1499, Daewha Maeul LG Apt. 101-601, Ilsan-Gu, Goyang City, Geonggi-Do (KR); Duck Hee Ryu, Goyang (KR); Jae Seong Kim, Goyang (KR); Yong Kim, Goyang (KR); Dae Hwan An, Goyang (KR)

(73) Assignee: Bo-Young Lee, Goyang, Gyeonggi-do (KR)

( * ) Notice: Subject to any disclaimer, the term of this patent is extended or adjusted under 35 U.S.C. 154(b) by 15 days.

(21) Appl. No.: 11/625,706

(22) Filed: Jan. 22, 2007

(65) Prior Publication Data

US 2007/0295099 A1    Dec. 27, 2007

(30) Foreign Application Priority Data

Jun. 26, 2006   (KR)   ................. 10-2006-0057258
Dec. 18, 2006   (KR)   ................. 10-2006-0129354

(51) Int. Cl.
*G01N 3/32*    (2006.01)
(52) U.S. Cl. .................. 73/808; 148/574; 148/570; 148/590
(58) Field of Classification Search ............ 73/808; 148/567, 570–571, 574, 590, 592, 655
See application file for complete search history.

(56) References Cited

U.S. PATENT DOCUMENTS 2,739,829 A * 3/1956 Cundiff et al. ............. 285/21.2
4,229,235 A * 10/1980 Matsuda et al. ............. 148/520
6,723,185 B1 * 4/2004 Elfving et al. ............. 148/510
2005/0210997 A1 * 9/2005 Lincoln et al. ........... 73/861.08
2006/0113010 A1 * 6/2006 Saitou et al. ................ 148/570

OTHER PUBLICATIONS

Kemppainen et al. "Advanced flaw production method for in-service inspection qualifcation mock-ups" Nuclear Engineering and Design vol. 224, pp. 105-117 (2003).*
Seki et al. "Development and testing of large-scale nuclear components and remote handling system in JAERI" Fusion Engineering and Design vol. 51-52, pp. 941-948 (2000).*

(Continued)

*Primary Examiner*—Lisa M Caputo
*Assistant Examiner*—Jonathan Dunlap
(74) *Attorney, Agent, or Firm*—IPLA P.A.; James E. Bame

(57) ABSTRACT

Disclosed is an apparatus and method for forming thermal fatigue cracks in a test piece for performance demonstration of nondestructive testing. The apparatus for forming thermal fatigue cracks includes a heating unit, having a conductive member attached around the outer surface of a pipe test piece and an induction heating coil disposed adjacent to the conductive member; a cooling unit, having a cooling water pump for forcibly supplying cooling water to the inner surface of the pipe test piece from a cooling water storage source and a cooling water hose; and a control unit for controlling operation of the heating unit and the cooling unit. Accordingly, thermal fatigue cracks similar to actual thermal fatigue cracks occurring during the operation of nuclear power plants or processing industry equipment are formed in a test piece, thereby assuring effective performance demonstration of nondestructive testing.

3 Claims, 6 Drawing Sheets

OTHER PUBLICATIONS

Takakura et al. "Development of elevated temperature structural design gide for Japanese demonstration breeder reactor" Nuclear Engineering and Design, vol. 155 (1995) pp. 559-570.*

Yamauchi et al. "Thermal fatigue behavior of a SUS304 pipe under longitudinal cyclic movement of axial temperature distribution". Thermomechanical fatigue behavior of materials: Second vol., ASTM STP 1263, 1996.*

Yamauchi et al. "Evaluation of creep-fatigue design methods by structural failure tests under thermal loads" Nuclear Engineering and Design, vol. 153 (1995) pp. 265-273.*

* cited by examiner

APPARATUS FOR FORMING THERMAL FATIGUE CRACKS

CROSS REFERENCES

Applicants claim foreign priority under Paris Convention and 35 U.S.C. § 119 to Korean Patent Application Nos. 10-2006-0057258 filed Jun. 26, 2006, and 10-2006-0129354 filed Dec. 18, 2006.

BACKGROUND OF THE INVENTION

1. Field of the Invention

The present invention relates to an apparatus and method for producing thermal fatigue cracks in a test piece for performance demonstration of nondestructive testing.

2. Description of the Related Art

Generally, in order to assure the integrity of nuclear power plant components and the stability of nuclear power plants, the safety of the components is periodically subjected to in-service inspection using nondestructive testing in consideration of the material, shape and predicted defects of the components.

Since in-service inspection of the nuclear power plants provides important results for estimating the lifetime of the plants and evaluating the safety of the components and an access to the nuclear power plants is limited, a nondestructive testing method having verified defect detection ability and high reliability should be used. In particular, the defect detection ability of an ultrasonic testing (UT) method and an eddy current testing (ECT) method has been verified to date using a simulation test piece and a mechanical process. However, there are many examples casting doubt on the ability to detect actual defects of such methods.

Accordingly, in USA, from the year of 2000, performance demonstration has been institutionalized to verify the defect detection ability of nondestructive testing, applied to nuclear components, using a test piece that simulates actual defects that are expected to occur in the nuclear components. Further, in Korea, from the year 2003, for performance demonstration of UT and ECT, the 'Korean Performance Demonstration System', which is centered on regulatory organizations and the owners of the power plants, has been developed.

The test piece for nondestructive verification required in ASME Section XI, Appendix VII, corresponding to the technical level applied to nuclear power plants, should include geometrical defects, implant defects, weld solidification cracks, lack of fusion, mechanical fatigue cracking, EDM notches and holes, thermal fatigue cracking, and intergranular stress corrosion cracking (IGSCC).

Moreover, techniques for producing thermal fatigue cracks, among the above defects, in a test piece, include three methods.

That is, exemplary are a first method of producing cracks comprising mounting a test piece to an autoclave and then repeatedly applying high/low temperatures to the test piece under appropriate tensile or compressive stress, a second method of producing cracks by repeatedly applying tensile and compressive stress while maintaining an appropriate temperature, and a third method of producing cracks only through repeated temperature change without the application of a mechanical load to the test piece.

However, since the test piece resulting from such a conventional thermal fatigue crack production method has properties of thermal fatigue cracks that are very different from those of actual thermal fatigue cracks occurring during operation of nuclear power plants or processing industry equipment, the effectiveness of performance demonstration of nondestructive testing cannot be reliably guaranteed.

SUMMARY OF THE INVENTION

Accordingly, the present invention has been made keeping in mind the above problems occurring in the related art, and an object of the present invention is to provide an apparatus for producing thermal fatigue cracks, which can guarantee the effectiveness of performance demonstration of nondestructive testing by producing, in a test piece, thermal fatigue cracks having properties similar to those of actual thermal fatigue cracks occurring in nuclear power plants or processing industry equipment during operation.

In order to accomplish the above objects, the present invention provides an apparatus for producing thermal fatigue cracks, which comprises a heating unit, including a conductive member attached around the outer surface of a pipe test piece and an induction heating coil disposed adjacent to the conductive member; a cooling unit, including a cooling water pump for forcibly supplying cooling water to the inner surface of the pipe test piece from a cooling water storage source and a cooling water hose; and a control unit for controlling the operation of the heating unit and the cooling unit.

Further, the pipe test piece may have a plurality of notches formed in the inner surface thereof.

Further, the pipe test piece may be provided at both ends thereof with respective flanges.

DESCRIPTION OF THE PREFERRED EMBODIMENT

Hereinafter, a detailed description will be given of the present invention with reference to the appended drawings.

Figure 1:
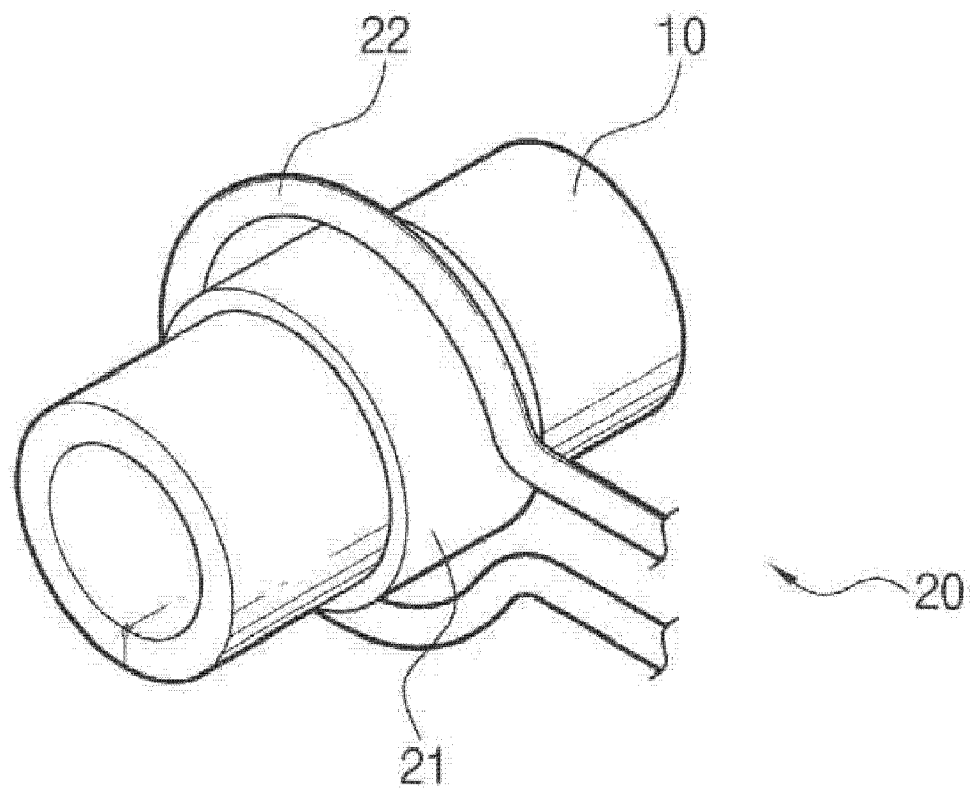
FIG. 1 is a partial perspective view illustrating the heating unit of an apparatus for forming thermal fatigue cracks, according to the present invention.
Figure 2:
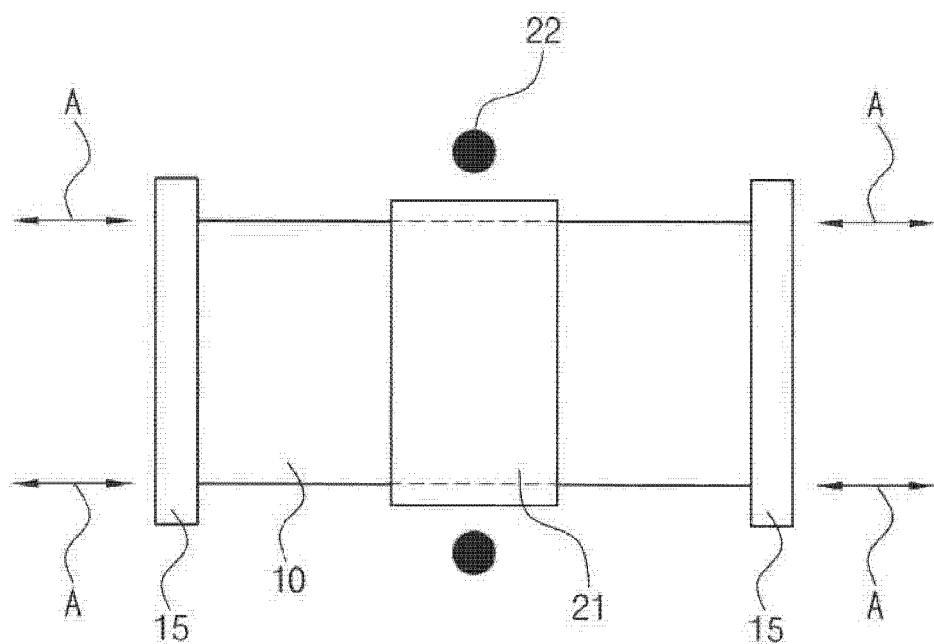
FIG. 2 is a schematic view illustrating a pipe test piece for use in the apparatus for forming the thermal fatigue cracks of the present invention, which is held at both ends thereof.
Figure 3:
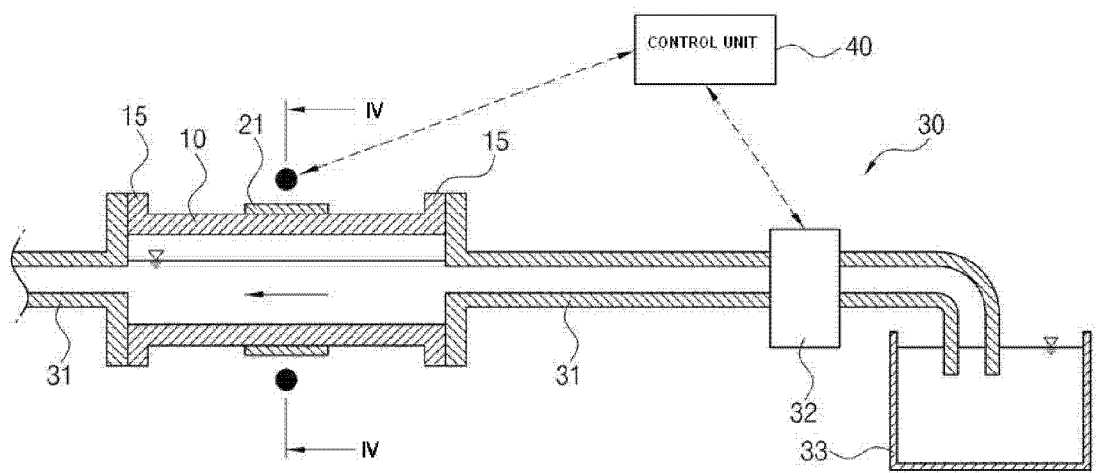
FIG. 3 is a schematic view illustrating the apparatus for forming the thermal fatigue cracks, according to the present invention.

FIGS. 1 to 3 schematically illustrate the apparatus for forming thermal fatigue cracks according to the present invention.

As illustrated in these drawings, the apparatus for forming thermal fatigue cracks according to the present invention comprises a heating unit 20 for applying heat to the outer surface of a pipe test piece 10, and a cooling unit 30 for forcibly cooling the inner surface 12 of the pipe test piece 10.

The heating unit 20 functions to apply predetermined heat to the outer surface of the pipe test piece 10 so as to create the thermal stress condition required for thermal fatigue cracking in the pipe test piece 10.

The pipe test piece 10 may be manufactured using actual pipe material for nuclear power plants or processing industry equipment, for example, STS 304, STS 316, STS 321, STS 347, STS 308, STS 309, Inconel 600, Inconel 690, Inconel 800, Inconel X750, Inconel 718, etc.

The heating unit 20 comprises a conductive member 21 formed of magnetic material attached around the outer surface of the pipe test piece 10, and an induction coil 22 spaced apart from the conductive member 21.

The induction coil 22 is connected with an external high-frequency current applier. When high-frequency current is applied to the induction coil 22 from the high-frequency current applier, a high-frequency magnetic field is formed in the induction coil 22. Due to the high-frequency magnetic field, in the conductive member 21 adjacent to the induction coil 22, heat is generated based on loss of eddy current or the loss of hysteresis, and thus the outer surface of the pipe test piece 10, to which the conductive member 21 is attached, is heated to a predetermined temperature.

Further, the inner surface of the pipe test piece 10 may be formed with a plurality of notches through turning. In this way, in the case where the plurality of notches is formed in the inner surface of the pipe test piece 10, the time period required for forming the thermal fatigue cracks can be decreased compared to when there are no notches.

Furthermore, the pipe test piece 10 should be held at both ends thereof in order to minimize external deformation thereof in a state in which thermal stress is applied to the outer surface thereof using the heating unit 20.

As illustrated in FIG. 2, the pipe test piece 10 is provided at both ends thereof with flanges 15, thus making it possible to more easily hold the pipe test piece 10.

That is, predetermined external force may be applied to the flange 15 of the pipe test piece 10, and furthermore, tensile and compressive stress A may be repeatedly applied to the flange 15, as seen in FIG. 2.

The flange 15 is mechanically connected, or is connected using a hydraulic or pneumatic device, so that both ends of the pipe test piece 10 can be held.

The cooling unit 30 functions to forcibly supply cooling water to the inner surface of the pipe test piece 10, thereby forming the cooling condition required for producing thermal fatigue cracks in the pipe test piece 10.

As illustrated in FIG. 3, the cooling unit 30 of the present invention comprises a cooling water storage tank 33 containing cooling water, a cooling water pump 32 for supplying cooling water from the storage tank 33 to the inner surface of the pipe test piece 10, and a cooling water hose 31 having one end connected to the pipe test piece 10 and the other end communicating with the cooling water storage tank 33 and the cooling water pump 32, and the cooling water hose 31 may be sealably connected to a flange 15 of the pipe test piece 10 using a packing.

In particular, in the present invention, the cooling water can be directly supplied to the inner surface of the pipe test piece 10 using the cooling unit 30, thus forming an interface similar to the thermal stratification caused by the temperature difference between a fluid flowing in the inner surface of the pipe test piece 10 and the inner surface of the test piece. As such, using the thermal stress (tensile or compressive stress) thus generated, it is possible to form thermal fatigue cracks similar to actual thermal fatigue cracks that occur in pipes of nuclear power plants or processing industry equipment during operation.

In addition, a control unit 40 for controlling the operation of the heating unit 20 and the cooling unit 30 is provided to appropriately control the conditions of the heating unit 20, such as the heating temperature and heating period, and the conditions of the cooling unit 30, such as the cooling water flow rate and cooling period.

The apparatus of the present invention thus structured is used as illustrated in FIG. 3.

As illustrated in FIG. 3, in a state in which both ends of the pipe test piece 10 are held by the flanges 15, the procedure, in which high-frequency induction heat is applied to the outer surface of the pipe test piece 10 using the heating unit 20 to thus realize predetermined high-frequency induction heating on the outer surface of the pipe test piece 10, and then the inner surface of the pipe test piece 10 is cooled using the cooling unit 30, is repeated, thereby realizing thermal fatigue cracks similar to thermal cracks generated in actual pipes.

A better understanding of the present invention may be obtained in light of the following experimental example, which is set forth to illustrate, but is not to be construed to limit the present invention.

EXPERIMENTAL EXAMPLE

The test piece for use in the present experimental example was made of STS 304 (O.D: 89 mm, t: 7.7 mm, yield strength: 41.8 kg/mm$^2$), widely used as a structural component of nuclear power plants.

The test piece had a length (l) of 500 mm. Further, in order to control the crack initiation position, an artificial notch was formed to a depth of 0.5 mm through turning at an angle of 55° in the circumferential direction of the test piece.

Figure 4:
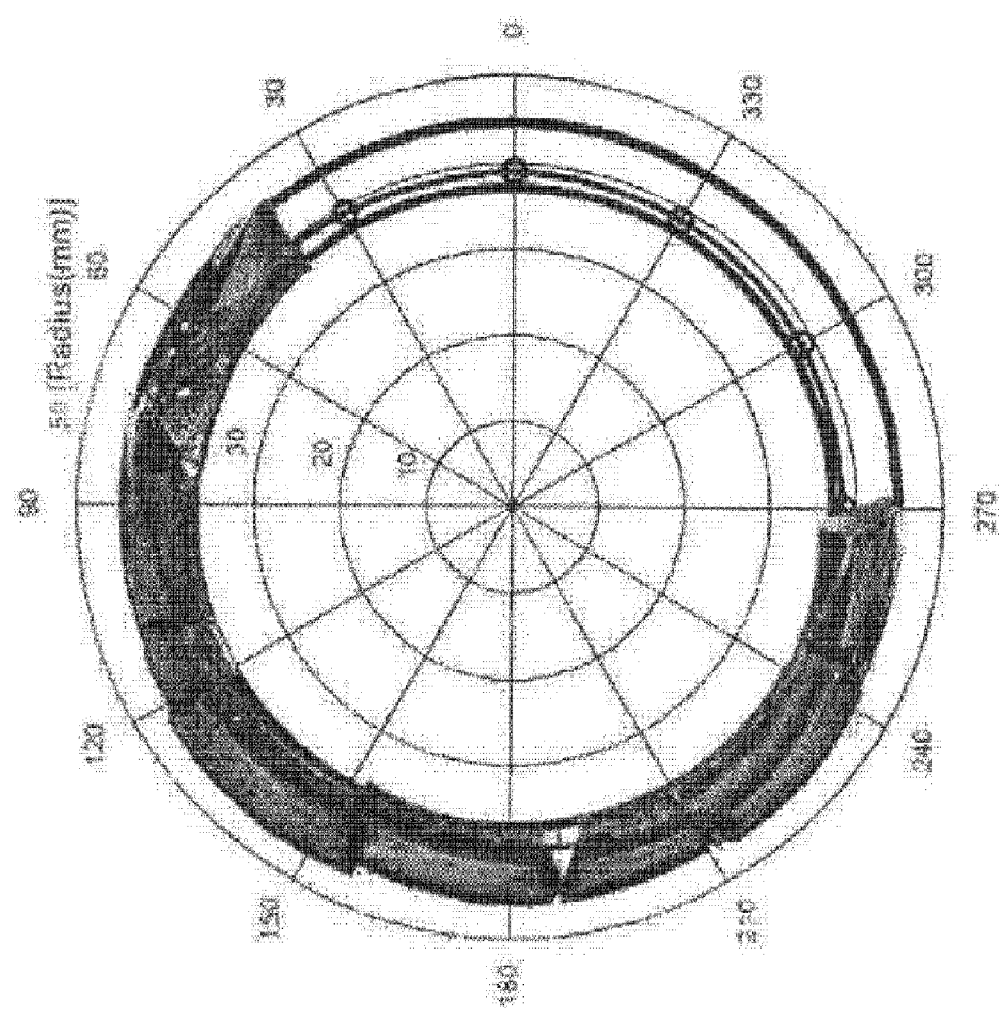
FIG. 4 is a photograph illustrating the section of the cracked portion of the pipe test piece, fractured along the line of IV-IV of FIG. 3.
Figure 5:
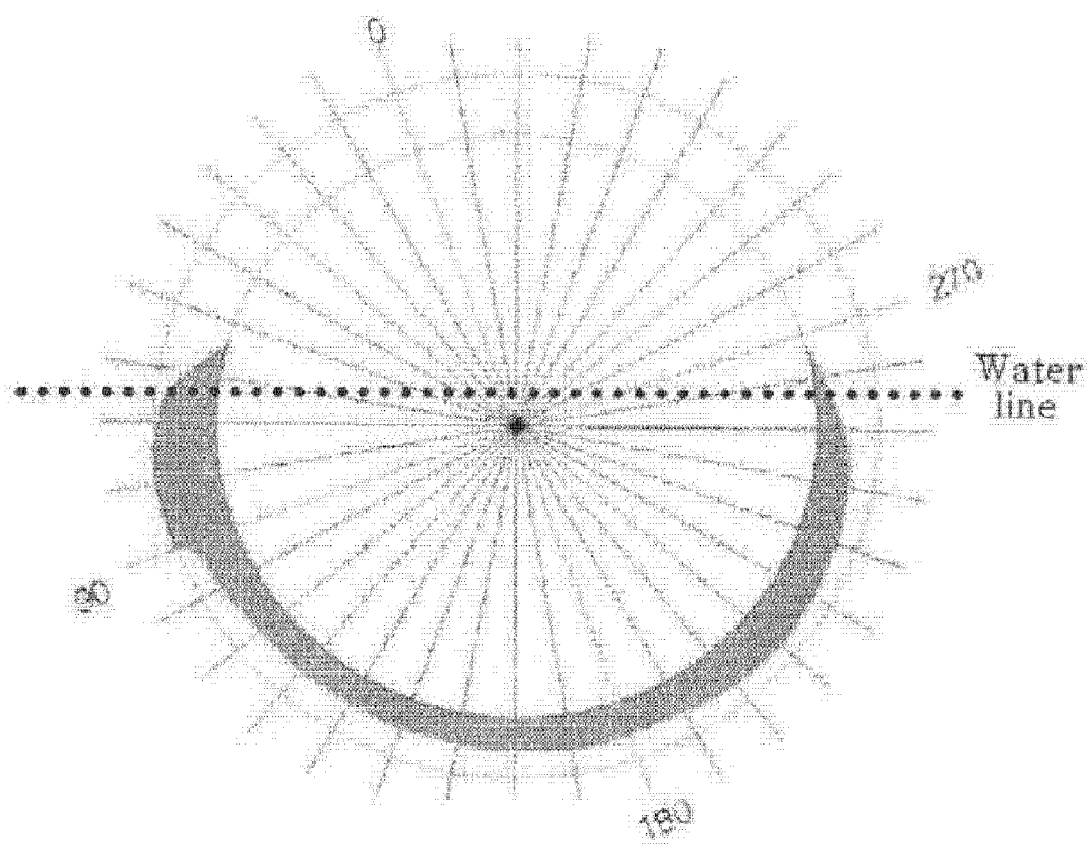
FIG. 5 is a view imaging the photograph of FIG. 4.

To determine the propagation rate and the propagation aspect of the thermal fatigue crack, induction heating for 2 min 40 sec and cooling for 20 sec were repeatedly applied to the pipe test piece through 25,000 cycles. The cracked portion was cut at intervals of 30°, cooled using liquid nitrogen, and fractured using a compressive tester. The fractured section was observed using an optical microscope and a scanning electron microscope (SEM). FIG. 4 illustrates the section of the cracked portion of the pipe, fractured along the line IV-IV of FIG. 3. The cracked section, which could not be clearly seen in the photograph, was imaged, and the depth thereof was measured using a CAD program. The imaged pipe section is illustrated in FIG. 5. The thermal fatigue crack propagated inward the pipe test piece in the region of 55°~270° (75°~295° relative to the top of the pipe) of the test piece. In the 90°~240° region of the pipe test piece, cracks were formed to almost the same depth. This was believed to be because the 90°~240° region of the test piece was affected by the temperature gradient caused during the thermal fatigue period, and thus the temperature distribution thereof was very similar to that of the section as given in Table 1 below.

In Table 1, the depths of cracks in a conventional test piece through a mechanical process measured using UT (control), and in an actual pipe (experimental group) were compared at intervals of 30° in the circumferential direction of the pipe.

TABLE 1

| | Crack Depth (mm) | |
|---|---|---|
| Angle(°) | UT (Control) | Actual Pipe (Experimental Group) |
| 0 | 1.950 | 0 |
| 30 | 2.222 | 0 |
| 60 | 3.199 | 4.08 |
| 90 | 3.171 | 7.7 (Perforated) |
| 120 | 2.901 | 4.05 |
| 150 | 2.313 | 4.05 |

TABLE 1-continued

| | Crack Depth (mm) | |
|---|---|---|
| Angle(°) | UT (Control) | Actual Pipe (Experimental Group) |
| 180 | 2.851 | 4.29 |
| 210 | 3.186 | 5.76 |
| 240 | 2.600 | 4.64 |
| 270 | 1.293 | 0 |
| 300 | 1.307 | 0 |
| 330 | 1.743 | 0 |

As is apparent from Table 1, the actual pipe had the heating temperature maintained at a predetermined level at the upper portion thereof and thus was in a continuous compressive stress state. On the other hand, the lower portion thereof was subjected to repeated expansion and contraction due to heating, but was not expanded as much as the upper portion of the pipe, and therefore the tensile stress gradient was considered to be repeated. Accordingly, the thermal fatigue cracks appeared and propagated at almost the same time along the temperature distribution line in the lower portion of the pipe. However, the 70°~90° region of the pipe, having the perforated crack, corresponded to a lead-in portion of the induction coil and thus had a temperature gradient relatively larger than the peripheral portions, to thus result in a steeper stress gradient. Thereby, the crack propagation rate was concluded to be slightly faster in the above region.

As seen in Table 1, as the results of UT using the conventional test piece through a mechanical process, the initial depth of cracking was not predicted and the shape of the cracks was different from that of the thermal fatigue cracks generated in the actual pipe, and therefore it was assumed that the UT could not reliably evaluate the depth of the cracking in the actual pipe.

Figure 6:
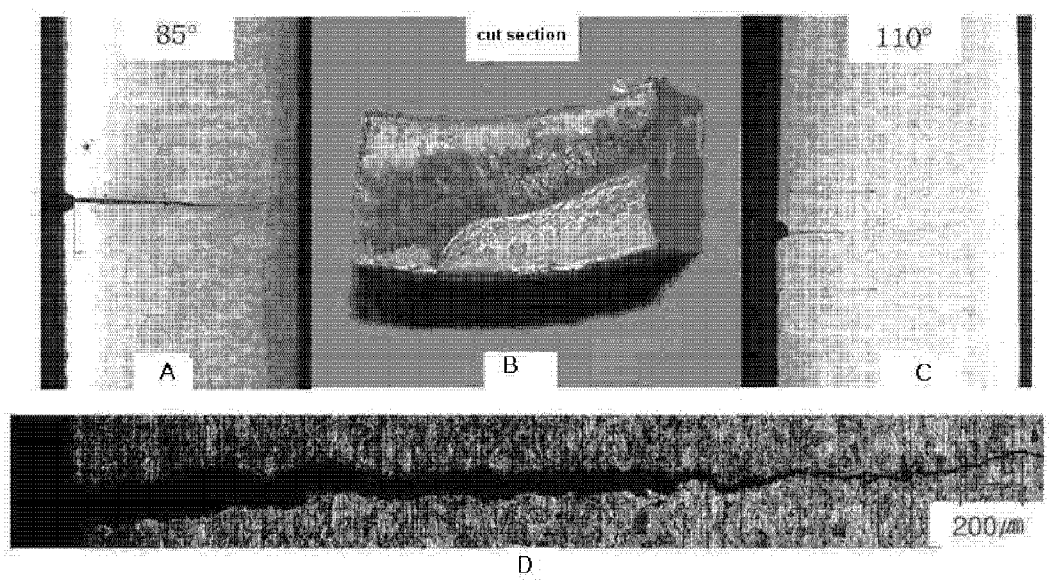
FIGS. 6A to 6D are photographs illustrating the cracks in the 85°~110° region of the pipe test piece.
Figure 7:
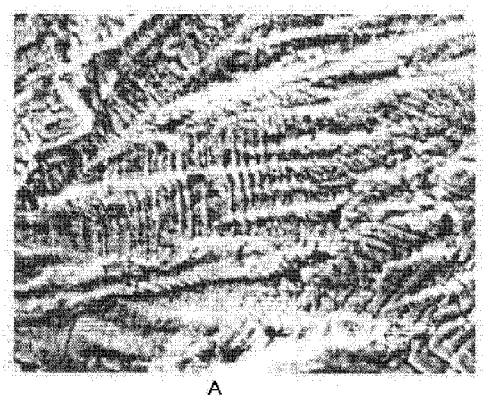
FIGS. 7A to 7D are photographs illustrating the cracked portion of FIG. 6B, which are taken from respective positions.
Figure 7:
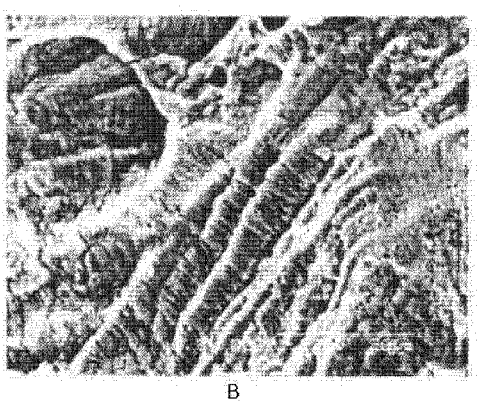
Figure 7:
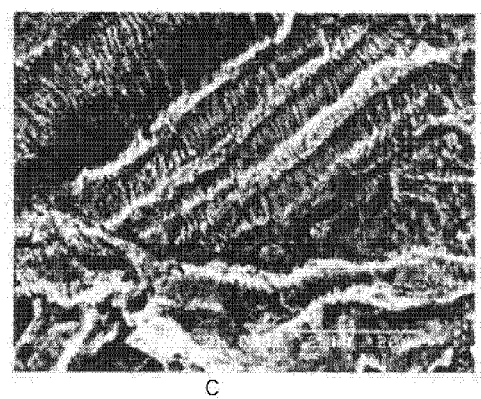
Figure 7:
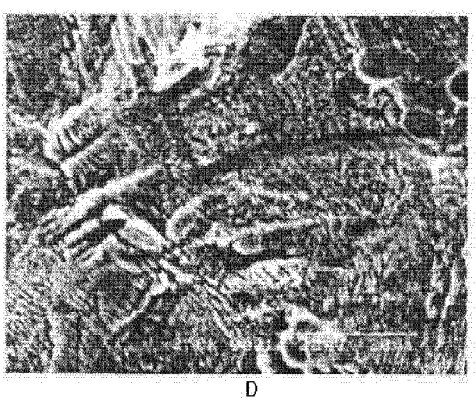

FIG. 6B illustrates the cracked portion of the pipe test piece ranging from 85° to 110°, FIG. 6A illustrates the section corresponding to the left side of FIG. 6B, that is, the section of the 85° region of the test piece, and FIG. 6C illustrates the section corresponding to the right side of FIG. 6B, that is, the section of the 110° region of the test piece.

From the section of the 85° region of the pipe test piece of FIG. 6A, the cracking could be seen to be propagated toward the outer surface of the test piece and thus perforated therethrough. Also, from the section of the 110° region of the test piece, the cracking could be seen to grow to a depth of 3.2 mm. The cracked portion, fractured using liquefied nitrogen, had a very clear fracture surface without predetermined deformation, but had scaling on the surface thereof, which was an oxide layer that forms on the surface of metal when heating it to a high temperature. Further, this surface, having a red brown color, was assumed to be severely contaminated. FIG. 6D is an optical photograph illustrating the cracked portion of FIG. 6C. As such, it could be seen that the notch portion, at which the crack initiated, was relatively broad, to a width of about 150 μm in a wedge shape, but the width thereof was drastically decreased to ones of μm at the tip of the crack. This was believed to be related to the stress gradient occurring upon the production of the thermal fatigue crack in the pipe. That is, due to the effects of compressive stress, generated in the upper portion of the pipe, and tensile stress, generated in the lower portion of the pipe upon cooling, shear cracks or slippages were initially generated, and then the growth to openings stably progressed to thus lead to the formation of striations, followed by alternating between brittleness and ductile fractures, thereby rapidly fracturing the pipe.

FIGS. 7A to 7D illustrate the fracture surface of FIG. 6B, observed using an SEM, in which exemplary were typical shapes of the specific striation of the fatigue surface, caused depending on whether the crack surface was opened or closed due to repeated loading upon crack propagation along the crack surface. The striations represented the advancement of cracks every cycle, and partially, could be used to confirm the crack propagation direction and rate. As the result of the analysis of FIG. 7A, in which the striation was clearly seen, the crack propagation rate was observed to be about 1 μm/cycle or more in the region of fast crack propagation. However, as a whole, as in FIG. 7C, the above rate was not realized, attributable to very small intervals.

As described hereinbefore, the present invention provides an apparatus for producing thermal fatigue cracks. According to the present invention, thermal fatigue cracks having properties similar to those of actual thermal fatigue cracks occurring in nuclear power plants or processing industry equipment during operation can be formed in a test piece, thereby realizing effective performance demonstration of nondestructive testing.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

What is claimed is:

1. An apparatus for forming thermal fatigue cracks in a non-magnetic pipe test piece, comprising:
   a heating unit, including a conductive member attached around an outer surface of the pipe test piece and an induction heating coil disposed adjacent to the conductive member;
   a cooling unit, including a cooling liquid pump for forcibly supplying cooling liquid to an inner surface of the pipe test piece from a cooling liquid storage source and a cooling liquid hose, wherein the pipe test piece has a plurality of notches formed in the inner surface thereof; and
   a control unit for controlling operation of the heating unit and the cooling unit, wherein the operation comprises heating temperature, heating period, cooling liquid flow rate, and cooling period, such that high and low temperatures are repeatedly applied to a portion of the pipe test piece surrounded by the conductive member so as to generate thermal fatigue cracking in the pipe test piece simulating actual thermal fatigue cracks occurring in a thermal system,
   wherein the heating period is a first period and the cooling period is a second period, wherein the heating period and the cooling period are repeated alternatingly for a predetermined cycles, and wherein the heating temperature, the cooling temperature, the first and second periods, the predetermined cycles are controlled so as to simulate actual thermal fatigue cracks.

2. The apparatus as set forth in claim 1, wherein the pipe test piece is provided at both ends thereof with respective flanges. and wherein periodic tensile and compressive stress is applied to the flanges by a hydraulic or pneumatic device.

3. The apparatus as set forth in claim 1, wherein the cooling liquid comprises water and liquefied nitrogen.

* * * * *